United States Patent
Fore

[19]

[11] Patent Number: 5,891,391
[45] Date of Patent: Apr. 6, 1999

[54] CLOTHING DEODORIZER FOR DEER HUNTERS

[76] Inventor: John C. Fore, 34,264 Hwy. 16 N., Denham Spring, La. 70726

[21] Appl. No.: 947,511

[22] Filed: Oct. 10, 1997

[51] Int. Cl.[6] ........................................ A61L 5/00
[52] U.S. Cl. ........................ 422/5; 422/124; 422/125; 424/402
[58] Field of Search ................ 422/5, 124, 125; 424/402

[56] References Cited

U.S. PATENT DOCUMENTS

| | | | |
|---|---|---|---|
| 2,251,058 | 7/1941 | Kirkman | 422/5 |
| 2,778,774 | 1/1957 | Buslik | 422/5 |
| 4,995,556 | 2/1991 | Arnold, III | 239/57 |
| 5,092,008 | 3/1992 | Okubo | 5/484 |
| 5,383,236 | 1/1995 | Sesselmann | 2/243.1 |
| 5,539,930 | 7/1996 | Sesselmann | 2/243.1 |
| 5,585,107 | 12/1996 | Vickers | 424/402 |

*Primary Examiner*—Krisanne Thornton
*Attorney, Agent, or Firm*—Reginald F. Roberts, Jr.

[57] ABSTRACT

A clothing deodorizer for deer hunters. The deodorizer includes a bag in which is placed the clothing to be deodorized of human odor. Within the bag a perforated container holds a granular material which can adsorb the human odor from the clothing. An object which can pulverize the granular material is placed in the container, so that as the bag is tumbled e.g. in a clothes dryer the object grinds the granular material into a powder which comes out through the perforations, contacts the clothing, and adsorbs the human odor exuded by the clothing.

15 Claims, 1 Drawing Sheet

CLOTHING DEODORIZER FOR DEER HUNTERS

BACKGROUND OF THE INVENTION

The present invention relates to deodorization. More particularly, the invention relates to the deodorization of clothing with respect to human odor.

A deer's primary defense is the sense of smell, which is extremely and extraordinarily keen. Deer hunters are always looking for ways to prevent a deer from picking up the human scent; keeping downwind of the deer, for example.

A more sophisticated approach is represented by U.S. Pat. Nos. 5,383,236 and 5,539,930, which disclose specialized clothing to be worn over a hunter's regular attire. The specialized clothing is impregnated with activated charcoal or other material which adsorbs the human odor exuded by the hunter.

While this approach represents an advance in the art, it has the disadvantage of requiring the purchase of specialized clothing. A second disadvantage is the requirement of periodic reactivation of the activated charcoal or other adsorbent.

It would be much more convenient and economical if the hunter's regular clothing could be deodorized before being worn for the hunt. The present invention provides an article and a method for doing this.

SUMMARY OF THE INVENTION

In general, the present invention in a first aspect provides a clothing deodorizer for deer hunters. The deodorizer comprises an outer container and a perforated inner container. A granular material capable of adsorbing human odor is disposed in the perforated inner container, together with an object capable of pulverizing the granular material. As the outer container is agitated, the granular material is converted into a powder which escapes through a perforation in the perforated inner container and contacts clothing disposed in the outer container.

In a second aspect the invention provides a method for adsorbing human odor from clothing. The clothing is contacted with a material which is capable of adsorbing human odor. A preferred way of carrying out the method comprises (a) disposing clothing in an outer container, (b) disposing within the outer container a perforated inner container which contains a granular material capable of adsorbing human odor, and an object capable of pulverizing the granular material, and (c) agitating the outer container to pulverize and convert the granular material into a powder which escapes through a perforation in the perforated inner container and contacts the clothing.

In a third aspect the present invention provides an article for adsorbing human odor from clothing. The article comprises first and second containers; a granular material capable of adsorbing human odor, for disposition in the second container; and an object capable of pulverizing the granular material, for disposition in the second container. The second container includes an opening therein, and is constructed and arranged for disposition in the first container. As the first container is agitated, the granular material is converted into a powder which escapes through the opening in the second container into the first container and contacts clothing disposed in the first container.

DETAILED DESCRIPTION OF THE INVENTION

Figure 1:
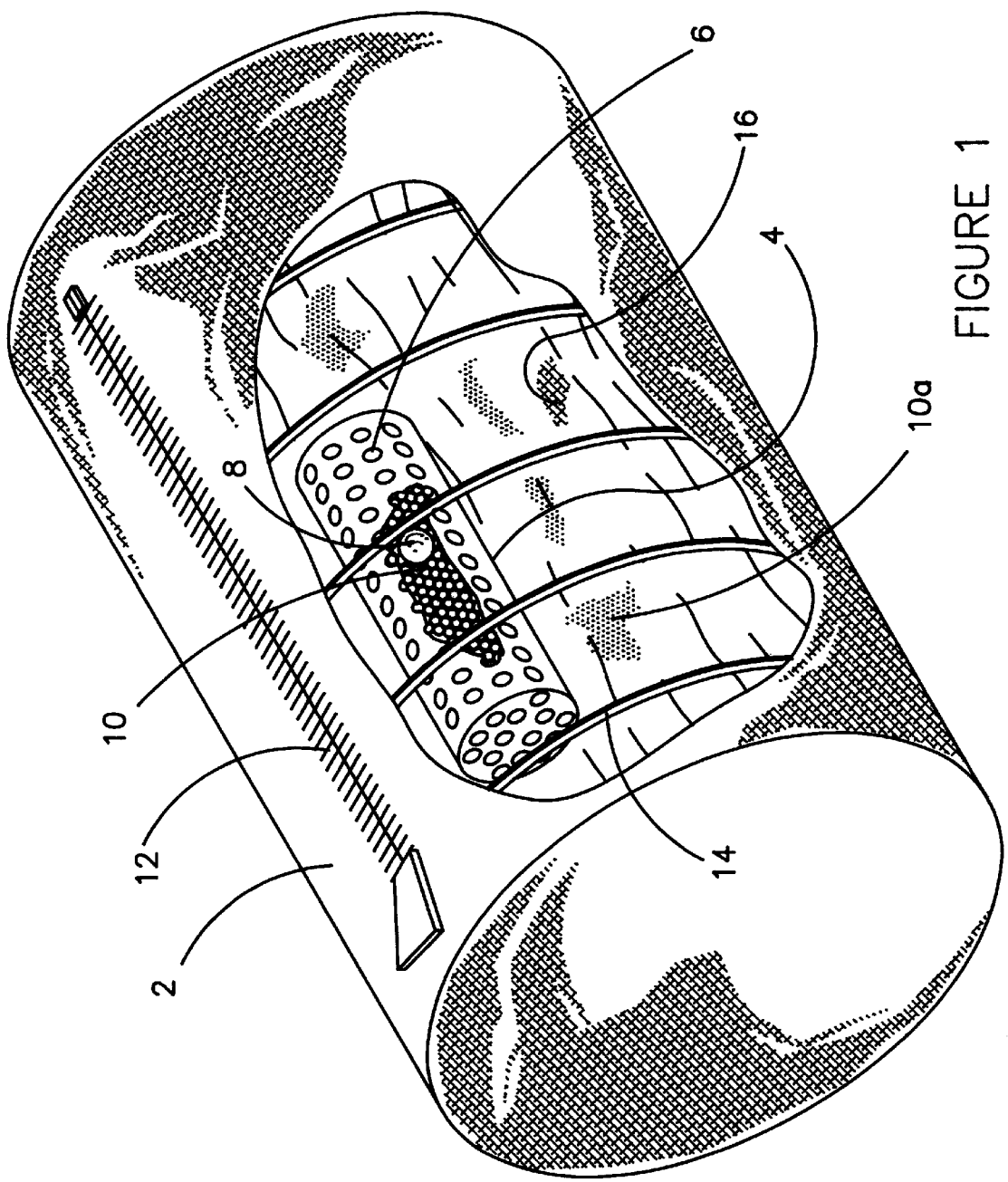
FIG. 1 is an isometric view of a clothing deodorizer for adsorbing human odor from clothing, made in accordance with the principles of the present invention, showing the clothing disposed within the clothing deodorizer.

The present invention provides an article and a method for deodorizing clothing with respect to human odor. The inventor believes that this object is achieved by adsorption of the odor by a material capable of adsorbing human odor. However, the inventor does not in any way limit his invention to any supposed mechanism such as adsorption. Hence, as used herein, the terms "adsorb", "adsorbing", and "adsorption" are defined to mean partial or total removal, whatever the mechanism may actually be.

More specifically, reference is made to FIG. 1, in in which is shown a clothing deodorizer for adsorbing human odor from clothing, made in accordance with the principles of the present invention, and showing the clothing disposed within the deodorizer.

The clothing deodorizer comprises an outer container 2 in which is disposed a refillable perforated inner container 4 having a plurality of perforations 6. An abrader 8 is disposed within the inner container 4, together with a granular material 10 which is capable of adsorbing human odor. A zipper 12 provides facile opening and closing of the outer container 2, which is preferably a bag made of a flexible material such as cloth, and held in an open, expanded configuration by a spring 14.

Clothing 16 to be deodorized is disposed within the outer container 2, the zipper 12 is used to close the container 2, and the outer container is agitated, preferably by tumbling in a clothes dryer. As the outer container 2 and its contents are agitated, the abrader 8 pulverizes the granular material 10, converting it into a powder 10a which escapes through peforations 6 which are sized smaller than the granulated material 10. The powder 10a escapes into the outer container 2, where it contacts the clothing 16 and adsorbs the human odor therefrom.

When the clothing 16 has been satisfactorily deodorized, the agitation is stopped, the zipper 12 is opened, and the clothing 16 is removed from the outer container 2. The outer container 2 may be compacted for transport by compressing the spring 14.

Materials capable of adsorbing human odor include activated charcoal, activated alumina, baking soda, zeolite, and similar substances; see, e.g., U.S. Pat. No. 5,539,930. Of these various materials, activated charcoal and activated alumina are preferred, and activated charcoal is most preferred. However, any granular material which is capable of adsorbing human odor and which is not potentially harmful lies within the scope of the present invention. More specifically, the inventor relies upon the doctrine of equivalents for the inclusion in his invention of any granular material and of all granular materials which is/are capable of adsorbing human odor, without doing harm to the user.

The present invention has the tremendous advantage over the prior art disclosed by U.S. Pat. Nos. 5,383,236 and 5,539,930 by not requiring the purchase or use of specialized clothing. Using the article and method of the present invention, a hunter need only treat his regular clothing in the manner described, over and over, an indefinite number of times.

I claim:

1. A clothing deodorizer for deer hunters, comprising:
   (a) an outer container;
   (b) a perforated inner container, disposed in the outer container;

(c) a granular material capable of adsorbing human odor, disposed in the inner container; and (d) an object capable of pulverizing the granular material, disposed in the inner container;

whereby, as the outer container is agitated, the granular material is converted into a powder which escapes through a perforation in the perforated inner container, to provide contact of the powder with clothing disposed in the outer container and adsorption of the human odor therefrom.

2. The clothing deodorizer of claim 1, wherein (e) the outer container is made of a flexible material; and (f) a spring is disposed in the outer container, to expand the outer container for maximum contact of the powder with the clothing.

3. The clothing deodorizer of claim 1, wherein the granular material is activated charcoal.

4. The clothing deodorizer of claim 1, wherein the perforation in the inner container is smaller than the particle size of the granular material.

5. The clothing deodorizer of claim 1, wherein the granular material is activated alumina.

6. A method for adsorbing human odor from clothing, the method comprising the steps of:

(a) disposing the clothing in an outer container;

(b) disposing within the outer container a perforated inner container which contains a granular material capable of adsorbing human odor, and an object capable of pulverizing the granular material; and (c) agitating the outer container to pulverize and convert the granular material into a powder which escapes through a perforation in the perforated inner container, contacts the clothing, and adsorbs human odor from the clothing.

7. The method of claim 6, wherein the granular material is activated charcoal.

8. The method of claim 6, wherein the granular material is activated alumina.

9. The method of claim 6, wherein the perforation in the perforated inner container is smaller than the particle size of the granular material.

10. The method of claim 6, wherein the outer container is made of a flexible material, and a spring is disposed in the outer container to expand the outer container for maximum contact of the powder with the clothing.

11. An article for adsorbing human odor from clothing, the article comprising:

(a) a first container;

(b) a second container, for disposition in the first container, the second container including an opening therein, and being smaller than the first container;

(c) a granular material capable of adsorbing human odor, for disposition in the second container; and (d) an object capable of pulverizing the granular material, for disposition in the second container;

whereby, as the first container is agitated, the granular material is converted into a powder which escapes through the opening in the second container into the first container, to provide contact of the powder with clothing disposed in the first container and adsorption of the human odor therefrom.

12. The article of claim 11, wherein (e) the first container is made of a flexible material; and (f) a spring is disposed in the first container, to expand the first container for maximum contact of the powder with the clothing.

13. The article of claim 11, wherein the granular material is activated charcoal.

14. The article of claim 11, wherein the opening in the second container is smaller than the particle size of the granular material.

15. The article of claim 11, wherein the granular material is activated alumina.

* * * * *